(12) United States Patent
Hossack

(10) Patent No.: US 6,409,667 B1
(45) Date of Patent: Jun. 25, 2002

(54) MEDICAL DIAGNOSTIC ULTRASOUND TRANSDUCER SYSTEM AND METHOD FOR HARMONIC IMAGING

(75) Inventor: John A. Hossack, Charlottesville, VA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/511,472

(22) Filed: Feb. 23, 2000

(51) Int. Cl.[7] .................................................. A61B 8/00
(52) U.S. Cl. ....................................... 600/443; 600/459
(58) Field of Search ................................. 600/437, 443, 600/458, 459, 463, 447; 310/321, 322, 328, 334, 365, 366; 73/625, 626

(56) References Cited

U.S. PATENT DOCUMENTS

| | | |
|---|---|---|
| 4,096,756 A | 6/1978 | Alphonse |
| 4,240,003 A | 12/1980 | Larson, III |
| 4,276,491 A | 6/1981 | Daniel |
| 4,354,132 A | 10/1982 | Borburgh et al. |
| 4,356,422 A | 10/1982 | van Maanen |
| 4,427,912 A | 1/1984 | Bui et al. |
| 5,115,809 A | 5/1992 | Saitoh et al. |
| 5,311,095 A | 5/1994 | Smith et al. |
| 5,410,205 A | 4/1995 | Gururaja |
| 5,415,175 A | 5/1995 | Hanafy et al. |
| 5,438,998 A | 8/1995 | Hanafy |
| 5,446,333 A | 8/1995 | Ishida et al. |
| 5,630,420 A | 5/1997 | Vaitekunas |
| 5,675,554 A | 10/1997 | Cole et al. |
| 5,685,308 A | 11/1997 | Wright et al. |
| 5,690,608 A | 11/1997 | Watanabe et al. |
| 5,724,976 A | 3/1998 | Mine et al. |
| 5,740,128 A | 4/1998 | Hossack et al. |
| 5,825,117 A | 10/1998 | Ossmann et al. |
| 5,920,972 A | 7/1999 | Palczewska et al. |
| 5,957,851 A | 9/1999 | Hossack |
| 5,984,869 A | 11/1999 | Chiao et al. |
| 6,005,827 A | 12/1999 | Hossack et al. |

OTHER PUBLICATIONS

Bouakaz et al., 2000, "Improved harmonic imaging with a new pahsed array transducer", ultrasound in Medicine and Biology, v 26 n SUPPL. 2 2000., p. A58.*

(List continued on next page.)

Primary Examiner—Marvin M. Lateef
Assistant Examiner—Ali M. Imam
(74) Attorney, Agent, or Firm—Brinks Hoffer Gilson & Lione; Craig A. Summerfield

(57) ABSTRACT

A transducer system and method for harmonic imaging is provided. At least one transducer element is provided. The transducer element comprises two stacked piezoelectric layers. Information from each of the layers is independently processed during one of a transmit event, a receive event, and both transmit and receive events. Information from the transducer element is provided to a filter. The filter isolates harmonic information for imaging. By providing a multi-layer transducer element with independent processing for each layer, a wide bandwidth transducer for harmonic imaging is provided. The null associated with most transducers at the second harmonic of a fundamental frequency is removed or lessened.

30 Claims, 2 Drawing Sheets

OTHER PUBLICATIONS

John A. Hossack et al., *Multiple Layer Transducers for Broadband Applications*; 1991 Ultrasonics Symposium; pp. 605–610.

John A. Hossack et al., Improving the Characteristics of a Transducer Using Multiple Piezoelectric Layers; IEEE Transactions on Ultrasonics, Ferroelectrics and Frequency Control, vol. 40, No. 2; pp. 131–139.

John A. Hossack et al., Improving Transducer Performance Using Multiple Active Layers; SPIE vol. 1733 (1992); pp. 284–296.

T. R. Gururaja et al., Medical Ultrasound Transducers with Switchable Frequency Bands Centered About $f_0$ and $2f_0$; 1997 IEEE Ultrasonics Symposium; pp. 1659–1662.

Jie Chen et al., DC–Biased Electrostrictive Materials and Transducers for Medical Imaging; 1997 IEEE Ultrasonics Symposium; pp. 1651–1658.

L. B. Russell et al., Thickness–Mode Modeling of Active Multi–Layered Piezoelectric Transducers and the Application to "SMART" Sensor Design; 1994 IEEE Ultrasonics Symposium; pp. 615–618.

\* cited by examiner

MEDICAL DIAGNOSTIC ULTRASOUND TRANSDUCER SYSTEM AND METHOD FOR HARMONIC IMAGING

BACKGROUND

This invention relates to a medical diagnostic ultrasound transducer system and method for harmonic imaging. In particular, a transducer system providing increased bandwidth for imaging with harmonic echoes from tissue, fluid or added contrast agents is provided.

Acoustic energy is transmitted into a patient at fundamental transmit frequencies. Acoustic energy is reflected off of tissue, fluid or other structures within the patient. The reflections include energy at the fundamental frequency band as well as energy generated at harmonic frequencies of the fundamental frequency band. The transducer converts the acoustic energy into an electrical signal.

Transducer bandwidth may limit the actual response, reducing the information content at harmonic or other frequencies. Manufacturing transducers with a 6 dB bandwidth or better exceeding 80% of the desired frequency range is difficult and expensive. For harmonic imaging, a 6 dB bandwidth exceeding 100 or 140% is preferably provided. For example, the transducer may transmit energy in a 3 to 5 MHz frequency range and receive information of interest in the 6 to 9 MHz range.

Larger bandwidth transducers are generally desirable for any type of ultrasonic diagnostic imaging. For example, transducers with a wide bandwidth are used for obtaining information at different fundamental frequencies during a same or different imaging sessions. Various techniques have been suggested for providing wide bandwidth transducers. For example, T. R. Gururaja et al in 'Medical Ultrasonics Transducers With Switchable Frequency Bands Centered about $f_0$ and $2f_0$', 1997 IEEE Ultrasonic Symposium, pp. 1659–1662, disclose an electrostrictive transducer element using two layers. A selected bias is applied to one layer, and a transmit waveform is applied to an electrode between the two layers for wide bandwidth transmission. As another example, J. Hossack et al. in Improving the Characteristics of A Transducer Using Multiple Piezoelectric Layers, IEEE Transactions On Ultrasonics, Ferroelectrics and Frequency Control, Vol. 40, No. 2, March 1993, disclose a two-layer piezoelectric single element transducer. A different waveform is applied to each of the layers on transmit, and phasing or delays are applied to signals from one of the layers relative to another layer on receive. As another example, different materials in a single layer transducer element may be used to extend the frequency range of the transducer.

U.S. Pat. No. 5,957,851, the disclosure of which is incorporated herein by reference, discloses an ultrasound transducer with multiple piezoelectric layers for use in harmonic imaging. Diodes or a transistor is used to isolate one layer from the other during transmit or receive. The same transducer is used to transmit at a fundamental frequency and receive at a harmonic frequency. For this passive switching system, the same transmit and receive processing is performed for each layer when each layer is being used.

BRIEF SUMMARY

The present invention is defined by the following claims, and nothing in this section should be taken as a limitation on those claims. By way of introduction, the preferred embodiments described below include a method and transducer system for harmonic imaging. At least one transducer element is provided. The transducer element comprises two stacked piezoelectric layers. The layers are stacked in the height or thickness direction which is perpendicular to an elevation-azimuth plane (i.e. azimuth is X direction, elevation is Y direction and range is Z direction). Information from each of the layers is independently processed during one of a transmit event, a receive event, and both of transmit and receive events. Information from the transducer element is provided to a filter. The filter isolates harmonic information for imaging. By providing a multi-layer transducer element with independent processing for each layer, a wide bandwidth transducer for harmonic imaging is provided. The null associated with most transducers at the second harmonic of a fundamental frequency is removed or lessened.

Further aspects and advantages of the invention are described below in conjunction with the preferred embodiments.

DETAILED DESCRIPTION OF THE PREFERRED EMBODIMENTS

A transducer system and method for harmonic imaging are discussed below. One or more of the transducer elements comprises multiple layers of piezoelectric material. As used herein, piezoelectic material comprises any material or device for converting acoustic energy into electrical signals and vice versa, such as piezoelectric ceramics or electrostatic moving membrane devices. During one or both of transmit and receive events, independent processing is provided for each of the layers. For example, a different waveform is provided to each of the layers of the transducer element during the transmit event. As another example, one of the electrical signals is delayed relative to another during the receive event. The independent processing provides for an increased bandwidth, maximizing the harmonic content passed through the transducer.

Figure 1:
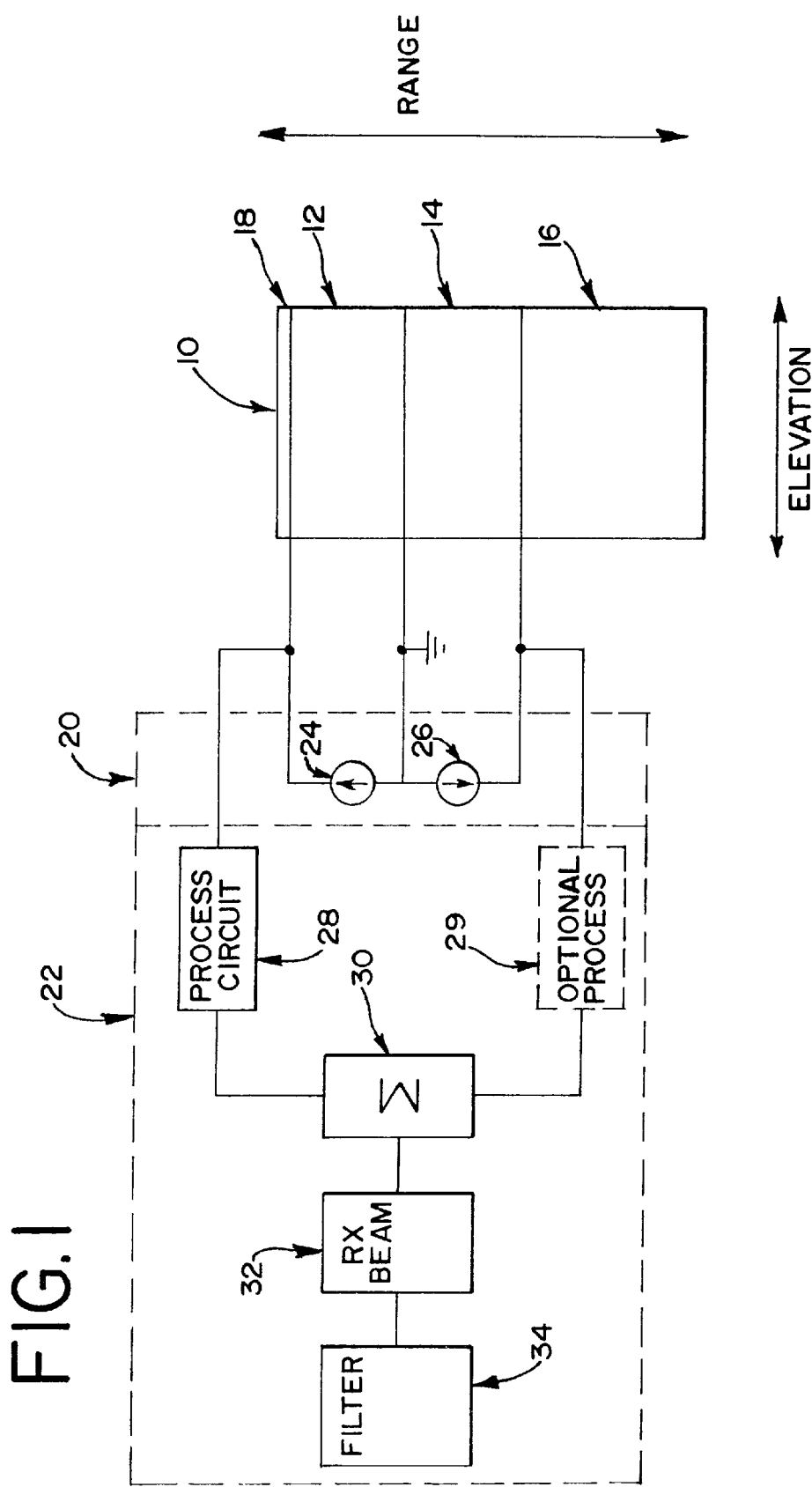
FIG. 1 is a block diagram of a medical diagnostic ultrasound transducer system for harmonic imaging.

FIG. 1 shows a block diagram of an ultrasound transducer system for harmonic imaging. The transducer system comprises a transducer element 10 connected with a transmitter 20 and a receiver 22. A different element may be connected with the transmitter 20 than is connected with the receiver 22.

The transducer element 10 comprises a top layer 12 and a bottom layer 14 of piezoelectric material, built layers between a backing layer 16 and a matching layer 18. The top and bottom layers 12 and 14 comprise a same or different piezoelectric material, such as a PZT/epoxy composite, a PVDF ceramic, Motorola HD3303, PZT 5H, or other piezoelectric material or ceramic. In alternative embodiments, the piezoelectric material comprises electrostatic micromachined devices. Each of the layers 12, 14 has a same or different geometry. For example, the same thickness is used for each layer, such as a ½ mm thickness. Other thicknesses may be used.

Preferably, the transducer element 10 is well matched by the matching layer 18 and the backing block 16. For example, the backing block 16 comprises tungsten-loaded epoxy or another backing block material. For example, other backing materials comprise various one of or combinations of metals (e.g., lead, copper), metal oxides (e.g., lead oxide, tungsten oxide), glass microballoons or spheres in a polymer, such as neoprene, polyurethane or epoxy. As another example, the matching layer 18 comprises a double matching layer comprising a high impedance matching layer (e.g., acoustic impedance about 9–10 MRayl) next to the PZT and a low impedance matching layer (e.g., Acoustic impedance about 2–2.5 MRayl). Single or triple matching layers are also possible. The matching layer may be eliminated. Given the broad bandwidth of the transducer element 10, the matching layer 18 may be selected as a function of higher frequencies (i.e. thinner rather than thicker). For example, the thickness of the matching layer 18 is less than the wavelength divided by four for the highest operating frequency of the transducer element 10. The bond layers between transducer components are preferably thin.

In one embodiment, an array of transducer elements and associated data paths shown in FIG. 1 are provided. The waves output by the transducer elements 10 either in transmit or receive are delayed and apodized relative to each of the elements 10 to generate a transmit or receive beam.

The transmitter 20 connected with the element 10 comprises first and second sources 24 and 26 of waveforms. Each or both sources 24 and 26 comprise an analog or digital transmit beamformer. For example, beamformers disclosed in U.S. Pat. Nos. 5,675,554, 5,690,608, 6,005,827, or 6,104,670, the disclosures of which are herein incorporated by reference, are used. Other sources of waveforms may be used, such as waveform generators or a waveform memory, digital-to-analog converter and amplifier. In alternative embodiments, a single source 24, 26 of waveforms is provided, and a delay or filter alters the waveform applied to one of the layers 12, 14 with respect to a waveform applied to the other layer 12, 14. Independent processing of the waveform is provided for the top layer 12 and for the bottom layer 14. Waveforms with different characteristics are applied to each layer 12, 14, but a same waveform may be applied in some situations.

The receiver 22 connected with the layers 12, 14 comprises a process circuit 28 connected to one of the layers and a summer 30, a receive beamformer 32 and a filter 34 operatively connected with the first and second layers 12 and 14. The receiver 22 comprises analog components, digital components or combinations thereof. The receiver 22 is preferably protected by standard diode clamping circuitry. This limits the voltage at the receiver input terminal to a safe level. Additionally, diode isolation circuitry is preferably included in the transmit circuitry which conducts during transmit events, but provides an open circuit during receive events, isolating the transmitter source impedance. The responses of the two transducer layers 12 and 14 are preferably preamplified separately. The second transducer layer 12 may be isolated from the first transducer layer 14 by a diode transistor, back-to-back diodes, or other combination of switches which are "on" when an applied voltage exceeds the diode 'turn on' voltage (e.g., about 0.7 volts). Other or no clamping circuitry, preamplification and isolation circuitry may be used.

In one embodiment, the process circuit 28 and summer 30 of the receiver 22 are incorporated into the housing of a transducer, reducing cable costs and improving signal quality. Other components may be incorporated into the transducer housing.

The process circuit 28 comprises an analog or digital delay. For delaying digital data, the process circuit 28 comprises registers and counters, but may comprise a processor or other digital device. The process circuit 28 has a fixed or programmable amount of delay. For simplicity, a fixed delay is used where the transducer 10 is well backed by the backing block 16. For example, the process circuit 28 provides a frequency dependent amount of delay, such as a frequency dependent phase filter (e.g., finite impulse response filter).

Alternatively, a frequency independent phase function is applied to the received signals received from the two layers. In one embodiment, the response of one layer 12, 14 is inverted (e.g., a phase rotation of 180 degrees) while the response of the other layer 14, 12 is non-inverted. Inverting and non-inverting pre-amplifiers are known. As an example, common in phase signals are applied during a transmit event to both layers, and a strong response at the fundamental is obtained. During the receive event, the response of one layer is inverted prior to summing, and consequently, a strong second harmonic response is obtained.

In the context of this application, phase and delay are used interchangeably. A delay corresponds to a linearly varying phase as a function of frequency. The phase function applied may be frequency dependent or frequency independent.

As shown, the process circuit 28 connects with the top layer 12, and no delay connects with the bottom layer 14. Information from the top layer 12 and the bottom layer 14 are independently processed. The responses of the two layers are summed after the relative delay or phasing (independent) processing and are then treated as one response. In alternative embodiments, a delay is provided for both the top and bottom layers 12 and 14, as shown by an optional process circuit 29. Other components, such as filters, processors or analog circuitry may be used on one or both of the separate data paths from the top and bottom layers 12 and 14 to provide independent processing. The independent processing may provide a same process or delay in some situations, but typically provides for a different process as described below.

The summer 30 receives the delayed information and comprises an analog or digital summer. For example, an operational amplifier is used for analog information, or a digital summation circuit is used for digital summation. Summing may occur, depending on implementation, in the analog or digital domain. If in the analog domain, the summer 30 may comprise a wire junction combining the currents from both layers. Other devices for combining the independently processed information from each of the layers 12 and 14 may be used.

The receive beamformer 32 receives the summed information and comprises analog and/or digital components. For example, the receive beamformer disclosed in U.S. Pat. No. 5,685,308, the disclosure of which is incorporated herein by reference, is used. The disclosed receive beamformer includes the filter 34. In alternative embodiments, the filtering function and the receive beamformer function are performed with separate components. Other receiver components, such as the summer 30 and/or process circuit 28, may be incorporated into the receive beamformer 32.

The filter 34 receives the beamformed data and comprises a digital signal processor, an application specific integrated circuit (ASIC), a finite impulse response filter, an infinite impulse response filter or other analog and/or digital components. In one embodiment, the filter 34 is included as part of the receive beamformer 32. The filter 34 provides highpass, bandpass or lowpass spectral response. The filter 34 passes information associated with the desired frequency band, such as the fundamental transmit frequency band or a harmonic of the fundamental frequency band. As used herein, harmonic comprises higher harmonics (e.g., second, third, . . . ), fractional harmonics (3/2, 5/3, . . . ), or subharmonics (1/2, 1/3, . . . ). The filter 34 may comprise different filters for different desired frequency bands or a programmable filter. For example, the filter 34 demodulates the signals to base band. The demodulation frequency is programmable selected in response to the fundamental center frequency or another frequency, such as a second harmonic center frequency. Other center frequencies may be used, such as intermediate frequencies. Signals associated with frequencies other than near the base band are removed by low pass filtering.

As an alternative or in addition to demodulation, the filter 34 provides band pass filtering. The demodulated and/or filtered signal is passed to an ultrasound signal processor as complex in-phase and quadrature signals, but other types of signals, such as radio frequency signals, may be passed.

The above described transducer system is used during one of a transmit event, a receive event or combinations thereof. In one embodiment, programmed excitation waveforms are independently processed and applied to each of the top and bottom layers 12 and 14 during a transmit event, and a different delay is applied to information received from each of the top and bottom layers 12 and 14 for independent processing during a receive event. Alternatively, information from a single layer is obtained during the receive event, or a single layer is used during a transmit event. In other alternative embodiments, switching mechanisms are provided to allow use of two layers during a transmit or receive event using a same process, such as applying a same transmit waveform to the top electrode of the top layer 12 and the bottom electrode of the bottom layer 14 and grounding the center electrode.

For transmit events, the two layers 12, 14 may be operated in parallel or without independent processing, since the bandwidth of interest is limited to the fundamental frequency. As used herein, independent processing comprises at least one component or act provided for one of the layers that is independent of a component or act being provided for another of the layers. The independent processing may be responsive to information from another layer.

In one embodiment, the independent processing applies a phase alteration to information to or from the top and bottom layers 12, 14. The phase of information for one layer is altered with respect to the phase of the other layer. The phase function is frequency dependent but may be independent of frequency. In transmit, the waveforms applied to each layer are in-phase or slightly out of phase (e.g., 90°). Generally, the received harmonic signal is substantially out of phase (e.g., around 180°) and therefore different phasing is used to obtain a meaningful response.

During transmission at fundamental frequencies, phased shaped waveforms are generated by the sources 24, 26 to produce the desired low frequency acoustic wave output by the transducer element 10. Alternatively, a high frequency waveform is output for using subharmonics.

The transducer element 10 may be represented as an equivalent circuit with two voltage sources, one for each layer 12, 14. The output of the transducer element 10 is obtained from the sum of the two sources. This is an application of the current superposition theorem.

Preferably, the relative phase of the two sources 24, 26 is measured for all frequency points of interests and then compensated for during transmission. During the transmission, the phase off-set due to the different propagation path from each layer 12, 14 cancels the applied phase, and the maximum output is obtained at all frequencies. Using a mathematical representation, suppose the output of a top layer is a phaser with a phase value of $\theta_1$ having a unit length, and the output of the second layer is a phaser with a phase value of $\theta_2$ also having a unit length. If the difference between $\theta_2$ and $\theta_1$ is applied to the input of the first layer, an in-phase output of two unit lengths is provided.

As described by Hossack et al. in Improving the Characteristics of A Transducer Using Multiple Piezoelectric Layers, IEEE Transactions On Ultrasonics, Ferro Electrics, and Frequency Control, Vol. 40, No. 2, March 1993 (the Hossack article), there is no unique solution for the waveforms to apply to each of the layers 12, 14 for obtaining a specified output response. In one embodiment, the waveforms requiring the smallest input amplitudes are used.

The force F of the output is obtained from the particle displacement, $A_F$. $F=sZ_F A_F$, where s is the Laplace operator and $Z_F$ is the mechanical impedance. In the Laplace domain for the multiple layer system, $\overline{F}=\overline{\beta}_1\overline{V}_1+\overline{\beta}_2\overline{V}_2+\overline{V}_1\ldots+\beta_N V_N$, where N is the number of layers and $\beta_1$ is the transfer function between the applied voltages and the output, and V is the applied voltage. $\beta_1$ may be obtained by measuring the force F when $V_1$ is set to 1 and $V_2$ is set to 0. $\beta_2$ may be evaluated similarly. Assuming the voltages applied to each layer are equal in terms of magnitude for a two-layer transducer, $\overline{F}=\overline{\beta}_1+\overline{\beta}_2$ or the $|F|<\theta=|\beta_1|<\theta_1+|\beta_2|<\theta_2$. The force output the absolute value of $F<\theta$ is maximized if $\theta_2=\theta_1$ as described above. The phase angle of $V_2$ is adjusted to compensate for the phase difference between $\beta_1$ and $\beta_2$. The desired result is obtained by setting $V_2=V_1<(\theta_1-\theta_2)$. The time domain excitation functions $V_1(t)$ and $V_2(t)$ are obtained using an inverse Fourier transform. As described in the Hossack article, once the desired acoustic output waveform is defined (e.g. a compact Gaussian pulse) and the transfer function (voltage in to pressure out) of the dual layer transducer established, the required voltage excitation functions to obtain the desired pulse shape are determined. In the Laplace (or Fourier) domain, the required output function is divided by the transfer function. Hence, the required value for $V_1$ is determined. $V_2$ is identical to $V_1$ except that the phase angle $(\theta_1-\theta_2)$ is applied. See pages 134–135 of the reference. In one embodiment, the phase angle correction is performed as a function of frequency. The phase angle correction may be linear as a function of frequency, corresponding to a simple time delay. Alternatively, the actual or an approximate non-linear function is used.

The independently generated or processed waveforms are provided to respective ones of the layers 12, 14 of the transducer element 10. In response, the transducer element 10 generates an acoustic waveform. The acoustic waveform propagates into the body, interacting with tissue and fluid and giving rise to harmonic information. Echo signals, including the harmonic signals, propagate back to the transducer element 10.

In the receive event, the top and bottom layers 12 and 14 generate electrical signals in response to the acoustic echoes. The information from each of the two layers 12, 14 is phase corrected and added. Additionally, filtering and amplification may be provided separately for each of the signals for each of the respective layers 12, 14. Since the relative phase characteristics of the layers 12, 14 are known, the frequency dependent phase difference between the signals is applied as a phase correction to one or both of the signals from the top or bottom layer 12, 14. After the delay or phase is adjusted, the information from the two layers is summed by the summer 30. The summed information is then beamformed. In one embodiment, the process circuit 28 provides a fixed delay. Alternatively, a dynamic delay is used. Additionally, the phase function may be dynamic or fixed. The phase function is different during receive events than the applied transmit function, such as inverting the signal.

Where second harmonic information is of interest, the delay is preferably applied to information from the top layer 12. In alternative embodiments, the delay is applied to the information from the bottom layer 14 or a combination of layers 12, 14. The amount of delay preferably corresponds to the sound propagation speed from the center of the top layer 12 to the center of the bottom layer 14 (e.g. typically equivalent to the propagation delay through one complete layer where both layers 12, 14 are equally thick). Since propagation speed is sometimes frequency dependent due to the finite transducer element dimensions relative to a wavelength, the process circuit 28 may provide delay as a function of frequency.

As described in the article by Hossack et al. referenced above, the phase relationship between the information from the two layers 12, 14 for receive events is the same or similar to the phase relationship between the two layers 12, 14 for transmit events. Since the response closely resembles the time delay function corresponding to the transmit time through the layers, the approximation may be used for applying an effective delay. Alternatively, for lower cost and somewhat lesser performance, a fixed phase inversion is applied to one of the layers. Application of the independent processing delay and summation of the information from the two layers provides a higher peak sensitivity and a bandwidth without a null at the second harmonic.

Figure 2A:
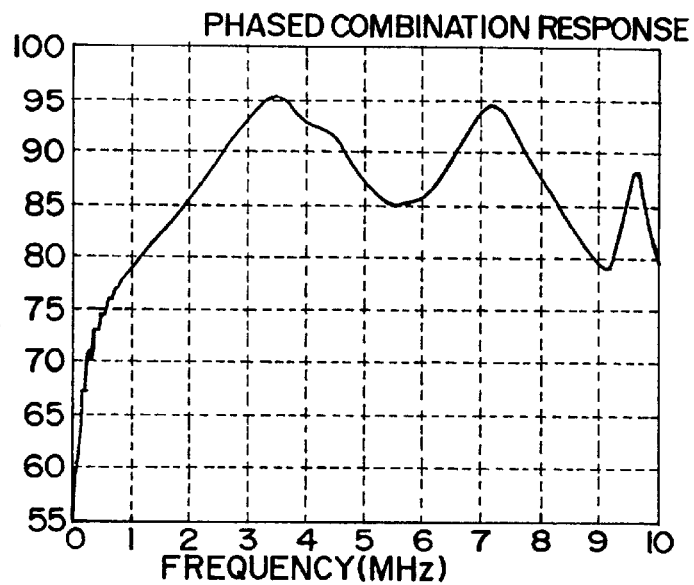
FIGS. 2A through 2C are graphical representations of a transducer spectral response for a multiple layer transducer, a top layer of the transducer, and a bottom layer of the transducer, respectively, of the transducer system of FIG. 1.
Figure 2B:
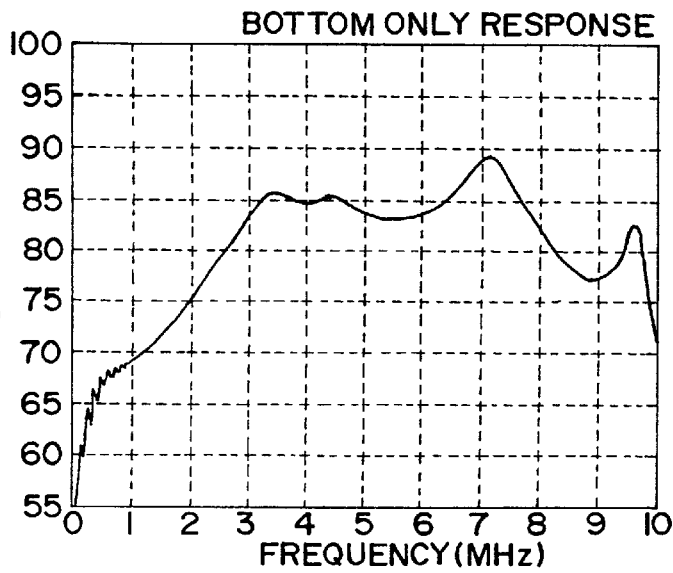
Figure 2C:
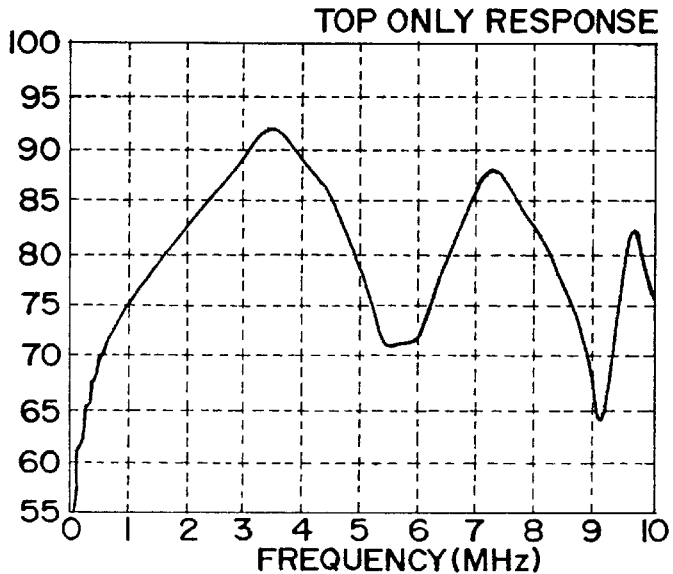

The information from each of the transducer layers 12, 14 is summed by the summer 30. The resulting sum provides for wide bandwidth information. FIG. 2A represents the spectral response of the independently processed and combined information. The response peaks at around 95 dB at 3⅓ MHz and around 7 MHz where the dB scale is offset as a result of the Fourier transform step. The dip between these two frequencies may be reduced as a function of the design of the transducer, including layer thickness, materials and geometry. For example, a lower impedance piezoelectric material is substituted, such a piezoelectric ceramic/epoxy composite for a pure piezoelectric ceramic material, and a heavier backing material may be used. FIGS. 2B and 2C represent the spectral response of the bottom and top layers 12, 14, respectively. As shown, a lesser magnitude is provided.

The combined information is received by the receive beamformer 32. The receive beamformer 32 obtains information from a plurality of transducer elements 10, applies focusing delays and apodization functions and generates in-phase and quadrature or radio frequency information representing one or more locations within a scanned body.

The in-phase and quadrature or radio frequency information is filtered by the filter 34. The filter 34 isolates or passes information at harmonics of the fundamental transmit frequencies. Information outside of that band is filtered or reduced. For example, the information at fundamental transmit frequencies is filtered and information at a second harmonic band is passed or isolated by the filter 34. The filtered information may be used in combination with other information or alone to generate an image on an ultrasound system. It is also possible to independently process separated fundamental and harmonic data and combine the information after signal detection to obtain a reduced speckle image. This compounding occurs over all or part of the image region.

The harmonic information is used for one of tissue imaging or contrast agent imaging. In tissue imaging, no additional contrast agent is added to the target during an imaging session. Only the characteristics of a tissue, including blood or other fluids, are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible. In this case, no contrast agent is introduced into the tissue at any time during the imaging session. Tissue harmonic images may provide a particularly high spatial resolution as a function of the echo generated from the tissue at harmonic frequencies. In particular, there may often be less clutter in the near field. Additionally, because the transmit beam is generated using the fundamental frequency, the transmit beam profile may be less distorted by a specific level of tissue-related phase aberration than would a transmit beam formed using signals transmitted directly at the second harmonic.

Imaging may be aided by the introduction of contrast agents. In contrast agent harmonic imaging, any one of a number of well known ultrasound contrast agents, such as microspheres, are added to the target or patient in order to enhance the nonlinear response of the tissue or fluid. The contrast agents radiate ultrasonic energy at the harmonic of an insonifying energy at fundamental frequencies.

Using the transducer system shown in FIG. 1 or other transducer systems described herein, optimal information is generated for harmonic imaging. This system may be used in combination with other harmonic imaging techniques, such as techniques utilizing different transmit or receive processing. For example, the transmit waveform output by each of the transducer elements 10 is shaped as a function of the applied electrical transmit waveforms to minimize energy at the second harmonic or any harmonic. The output transmit waveform from each element 10 may be predistorted to account for any propagation or system nonlinearities. As another example, delays and apodization from one element 10 to another element 10 are altered to provide a line focus or a more spread beam. The relative phasing associated with each beam transmitted may alternate as a function of scan line and then data from different beams is combined. Other harmonic imaging techniques may also be used.

The broad bandwidth provided may allow the transducer system to be used with new or previously difficult to implement transmit or receive techniques. For example, the symbol rate in an acoustic code for a coded excitation is limited by the ability of the transducer to provide sufficient bandwidth. The transducer system described herein may be used for coded excitations, such as disclosed in U.S. Pat. No. 5,984,869, the disclosure of which is herein incorporated by reference.

While the invention has been described above by reference to various embodiments, it will be understood that many changes and modifications can be made without departing from the scope of the invention. For example, a third or fourth layer may be used for each transducer element. Different independent processes may be provided for information associated with either transmit or receive events for each layer. The piezoelectric materials for each of the layers may be of different and the layer dimensions (especially thickness) may be different. One or more of the piezoelectric layers may vary in thickness, such as the plano-concave layers described in U.S. Pat. Nos. 5,415,175 and 5,438,998, the disclosures of which are incorporated herein by reference. Additionally, the concept may extend to 1.5 and 2 D arrays. Furthermore, not all the elements in the array need to contain multiple piezoelectric layers. For example, in a 1.5 D array, only the center elements have multiple piezoelectric layers.

It is therefore intended that the foregoing detailed description be understood as an illustration of the presently preferred embodiments of the invention, and not as a definition of the invention. It is only the following claims, including all equivalents that are intended to define the scope of the invention.

What is claimed is:

1. A medical diagnostic ultrasound transducer system for harmonic imaging, the transducer system comprising:
    at least one transducer element comprising first and second stacked layers;
    a first path connected with the first layer;
    a second path connected with the second layer, the first and second paths operable to independently process information during one of: a transmit event, a receive event and combinations thereof; and
    a filter operable to pass information from the at least one transducer element that is at a harmonic of a fundamental transmit frequency and operable to filter information at the fundamental transmit frequency.

2. The system of claim 1 wherein the at least one transducer element comprises an array of transducer elements comprising first and second layers.

3. The system of claim 1 wherein the first and second paths are operable to independently process information during the transmit event.

4. The system of claim 3 wherein the first and second paths comprise first and second waveform source, respectively.

5. The system of claim 1 wherein the first and second paths are operable to independently process information during the receive event.

6. The system of claim 5 further comprising an summer operatively connected with the first and second paths; and
    wherein the first path comprises a delay.

7. The system of claim 1 wherein the first and second paths are operable to independently process information during the transmit and receive events.

8. The system of claim 1 wherein the filter comprises a bandpass filter.

9. A medical diagnostic ultrasound method for harmonic imaging, the method comprising the acts of:
    (a) independently processing, during one of: a transmit event, a receive event and combinations thereof, information associated with first and second stacked layers of a transducer element; and
    (b) isolating information at a harmonic of a fundamental transmit frequency from the information from the first and second layers.

10. The method of claim 9 further comprising performing (a) for each of a plurality of arrayed two layer transducer elements.

11. The method of claim 9 wherein (a) comprises independently processing the information during the transmit event.

12. The method of claim 11 wherein (a) comprises:
    (a1) providing a first waveform to the first layer; and
    (a2) providing a second waveform to the second layer.

13. The method of claim 9 wherein (a) comprises independently processing the information during the receive event.

14. The method of claim 13 wherein (a) comprises delaying the information from the first stacked layer relative to the information from the second layer; and
    further comprising:
        (c) adding the information from the first and second layers.

15. The method of claim 9 wherein (a) comprises independently processing the information during the transmit and receive events.

16. The method of claim 9 wherein (c) comprises bandpass filtering the information.

17. The method of claim 9 further comprising:
    (c) transmitting acoustic energy from the transducer element into a target, wherein the target is free of added contrast agent during an entire imaging session.

18. The method of claim 9 further comprising:
    (c) transmitting acoustic energy from the transducer element into a target comprising added contrast agents.

19. A medical diagnostic ultrasound transducer system for harmonic imaging, the transducer system comprising:
    an array of transducer elements comprising first and second stacked layers;
    a plurality of first paths each connected with a respective first layer of one of the array of transducer elements; and
    a plurality of second paths each connected with a respective second layer of one of the array of transducer elements, the first and second paths operable to independently process information during one of: a transmit event, a receive event and combinations thereof.

20. The system of claim 19 wherein the first and second paths are operable to independently process information during the transmit event.

21. The system of claim 20 wherein the first and second paths comprise first and second waveform sources, respectively.

22. The system of claim 19 wherein the first and second paths are operable to independently process information during the receive event.

23. The system of claim 22 further comprising a plurality of summers each operatively connected with one of each of the first and second paths; and
    wherein each of the first paths comprises a delay.

24. The system of claim 19 further comprising a filter operable to pass information from the array of transducer elements that is at a harmonic of a fundamental transmit frequency and operable to filter information at the fundamental transmit frequency.

25. The system of claim 1 wherein the first path implements a frequency dependent phase function.

26. The system of claim 1 wherein the first path implements a frequency independent phase function which is different from a phase function applied to the second layer.

27. The system of claim 1 wherein the first path implements a frequency dependent amplitude function.

28. The system of claim 1 wherein the first path implements a different phasing relative to second layer during a transmit event than during a receive event.

29. The method of claim 9 further comprising:
(c) defining a desired acoustic output waveform;
(d) determining excitation waveforms as a function of the desired acoustic output waveform and a transfer function of the first and second layers.

30. The system of claim 5 further comprising an summer operatively connected with the first and second paths; and wherein the first path comprises a phase adjuster.

* * * * *